United States Patent [19]

Nolte et al.

[11] Patent Number: 4,865,741

[45] Date of Patent: Sep. 12, 1989

[54] SEPARATION OF OIL INTO FRACTIONS OF ASPHALTENES, RESINS, AROMATICS, AND SATURATED HYDROCARBONS

[75] Inventors: David G. Nolte, Houston; Edwin L. Collings, Jr., Sugar Land, both of Tex.

[73] Assignee: Texaco Inc., White Plains, N.Y.

[21] Appl. No.: 289,092

[22] Filed: Dec. 23, 1988

[51] Int. Cl.$^4$ .............................................. B01D 15/08
[52] U.S. Cl. .................................... 210/635; 210/656; 210/659; 585/825
[58] Field of Search ..................... 210/635, 656, 198.2, 210/659; 585/822, 825; 208/323, 333, 336; 588/833, 838

[56] References Cited

U.S. PATENT DOCUMENTS

| | | | |
|---|---|---|---|
| 2,936,282 | 5/1960 | Paris | 585/825 |
| 3,849,300 | 11/1974 | Martin | 210/635 |
| 4,341,634 | 7/1982 | Matsushita | 210/656 |
| 4,787,983 | 11/1988 | DiFoggio | 210/656 |
| 4,802,986 | 2/1989 | Hayes | 210/635 |

*Primary Examiner*—Ernest G. Therkorn
*Attorney, Agent, or Firm*—Jack H. Park; Kenneth R. Priem; Harold J. Delhommer

[57] ABSTRACT

The invention is a method of group type separation of whole oils and bitumen by high performance liquid chromatography into fractions of asphaltenes, resins, aromatics, and saturated hydrocarbons. A multistep process is involved wherein the oil is initially solvated with a three part solvent mixture of methanol, acetone, and choroform. The solvated oil mixture is injected with a mobile phase into a cyano bonded phase column which will retain asphaltenes and resins, and pass through aromatics and saturated hydrocarbons. The unretained aromatics and saturated hydrocarbons are then injected into a silica column which will retain aromatics and pass through saturated hydrocarbons. Saturated hydrocarbons are recovered as they pass through the silica column. The resins, asphaltenes, and aromatics are recovered from the columns by a displacement material.

11 Claims, No Drawings

SEPARATION OF OIL INTO FRACTIONS OF ASPHALTENES, RESINS, AROMATICS, AND SATURATED HYDROCARBONS

BACKGROUND OF THE INVENTION

This invention relates to hydrocarbon separation. More particularly, the invention concerns a process for separating oil and bitumen into group type fractions of asphaltenes, resins, aromatics and saturated hydrocarbons by high performance liquid chromatography.

Although there are an abundance of processes known to separate classes of hydrocarbons, accurate separation of whole oils and bitumens for geochemistry purposes was previously limited to open column separation methods. Such methods were complex and quite lengthy, involving up to several days to complete the separations.

High performance liquid chromatography (HPLC) methods were then developed for the group type fractionation of whole oils and bitumens. However, these methods require prior precipitation of the asphaltene fraction. Asphaltene precipitation is usually accomplished using a large excess of a linear saturated hydrocarbon, such as n-butane, n-pentane, n-hexane, and n-heptane. The solute is then fractionated into saturated hydrocarbon, aromatic hydrocarbon and resin groups by HPLC.

An inherent accuracy problem exists with such separation methods. The solubility of asphaltenes is sensitive to both the temperature and volume of the precipitating media. High molecular weight saturated hydrocarbons, aromatic hydrocarbons, and resins are sensitive to the same solubility effects as asphaltenes with the added problem of their being encapsulated or sequestered by the asphaltene precipitate. This precludes the recovery of some high molecular weight saturated hydrocarbons, aromatics, and resins. Such loss is unfortunate because valuable biomarker information is often contained in such high molecular weight hydrocarbon fractions.

SUMMARY OF THE INVENTION

The invention is a method of group type separation of whole oils and bitumen by high performance liquid chromatography into fractions of asphaltenes, resins, aromatics, and saturated hydrocarbons. A multistep process is involved wherein the oil is initially solvated with a three part solvent mixture of methanol, acetone, and chloroform. The solvated oil mixture is injected with a mobile phase of freon or an alkane into a cyano bonded phase column which will retain asphaltenes an resins and pass through saturated hydrocarbons and aromatics. The unretained aromatics and saturated hydrocarbons are then injected into a silica column which will retain aromatics and pass through saturated hydrocarbons.

The saturated hydrocarbons are recovered as they are passed through the silica column. The resins are recovered by displacing the resins from the cyano column with a polar displacement material. The asphaltenes are recovered by displacing the asphaltenes from the cyano column with a displacement material having a greater polarity than the resin displacement material. The aromatics are recovered by displacing the aromatics from the silica column with a displacement material.

DETAILED DESCRIPTION

The problem of inconsistent asphaltene precipitates and the sequestration of high molecular weight non-asphaltene fractions by asphaltene precipitation is solved by the instant invention. Whole oil or bitumen is first solvated by a strong three part solvent mixture and injected with a mobile phase into an HPLC instrument containing a cyano bonded phase column and a silica column. The three part solvent mixture responsible for carrying the asphaltenes into the HPLC interacts with the cyano column causing the cyano column to retain asphaltenes. The cyano column adsorbs the methanol and acetone, causing the remaining mixture to fractionate. The asphaltenes precipitate. The resins are adsorbed by the cyano column, and the remaining components are swept by the mobile phase out of the cyano column into the silica column.

The invention comprises a multistep method, the first step of which is solvating the oil or bitumen with a three part solvent mixture of about 5% to about 25% methanol, about 5% to about 25% acetone, and about 60% to about 80% chloroform, more preferably about 13% to about 17% methanol, about 13% to about 17% acetone, and about 66% to about 75% chloroform.

The solvated oil mixture is injected with a mobile phase of freon or an alkane having about 5 to about 8 carbon atoms, preferably hexane. This injection is generally carried out by placing said solvated oil mixture in a sample loop and injecting the contents of the sample loop as a slug following and preceding the mobile phase.

The solvated oil mixture is injected with the mobile phase into a cyano bonded phase column under retention conditions which will retain asphaltenes and resins, and pass through aromatics and saturated hydrocarbons. The aromatics and saturated hydrocarbons unretained by the cyano column are injected under retention conditions into a silica column which will retain aromatics and pass through saturated hydrocarbons.

The saturated hydrocarbons unretained by the silica column are recovered and the other fractions are recovered by displacement from the columns. The resins are recovered first by displacing the resins from the cyano column with a polar displacement material. The asphaltenes are recovered by displacing the asphaltenes from the cyano column with a displacement material having a greater polarity than the resin displacement material. The aromatics are recovered by displacing the aromatics from the silica column with a displacement material.

Preferably, the cyano column is selected so that the resins will be retained for a time sufficient to separate the resins from the unretained aromatics and saturated hydrocarbons. The resins may be later eluted from the cyano column or displaced by backflushing the cyano column with a displacement material, preferably a displacement material comprising a mixture of hexane and chloroform. Most preferably, the mixture comprises about 92% to about 96% hexane and about 4% to about 8% chloroform.

After resin recovery, the asphaltenes may be displaced from the cyano column by backflushing with a displacement material preferably having the composition of the three part solvent mixture. The aromatics are preferably displaced by backflushing the silica column with chloroform. Since chloroform deactivates the silica column, the silica column must be regenerated after each use. Preferably regeneration is accomplished by injecting the same compound previously injected as the mobile phase with the solvated oil mixture. If hexane was injected as the mobile phase, then hexane should be employed to reactivate the silica column.

Additional information can be gathered by weighing the recovered fractions of asphaltenes, resins, aromatics, and saturated hydrocarbons and comparing that weight with the weight of the starting sample. This will yield the fraction of the starting sample boiling lower than n-$C_{11}$ lost during any solvent removal from the recovered fractions. Analysis has indicated that essentially 100% of all four fractions boiling above n-$C_{11}$ are recovered by the invention method. However, the standard method of removing solvents from collected fractions by rotary evaporation at about 32° C. and 25 inches Hg vacuum causes some loss of fractions boiling lower than n-$C_{11}$.

This invention method has been tested and compared with other open column and HPLC methods of separation. Because of the novel step of injecting asphaltenes, and not first precipitating asphaltenes, greater recovery of high molecular weight components of resin, aromatic and saturated hydrocarbon fractions was achieved. Higher purity fractions were also obtained with a substantial reduction in manpower and total analysis time over open column methods.

Instrumentation employed consisted of an HPLC system with three Valco electric valves. A 10-port valve, Valco Model No. EC10W was configured for sample insertion and backflushing, while two 6-port valves, Valco Model No. EC6W, were used to individually isolate the cyano column and the silica column.

The silica material employed was a silica sold under the trademark RSIL Silica by Alltech, Inc., sized at 10 microns, irregularly shaped. The silica was hand packed into a column of 10 mm inner diameter by 200 mm long. In later use, the silica column was lengthened to 500 mm for better separation.

The cyano material employed was an alkyl nitrile sold under the trademark RSIL CN by Alltech, Inc., sized at 10 microns, irregularly shaped. The cyano material was hand packed into a column of 10 mm inner diameter by 200 mm long. In later use, the cyano column was lengthened to 250 mm for better separation.

Except for the manual loading of the sample into a sample loop of the HPLC system, each run was made unattended. Runs were completed in slightly less than 1 hour, including the reactivation of the silica column.

Many other variations and modifications may be made in the concepts described above by those skilled in the art without departing from the concepts of the present invention. Accordingly, it should be clearly understood that the concepts disclosed in the description are illustrative only and are not intended as limitations on the scope of the invention.

What is claimed is:

1. A method of group type separation of oil or bitumen by high performance liquid chromatography, which comprises:
    solvating the oil with a three part solvent mixture of about 5% to about 25% methanol, about 5% to about 25% acetone, and about 60% to about 80% chloroform;
    injecting the solvated oil mixture with a mobile phase of freon or an alkane having about 5 to about 8 carbon atoms into a cyano bonded phase column under retention conditions which will retain asphaltenes and resins, and pass through unretained saturated hydrocarbons and aromatics;
    injecting the unretained aromatics and saturated hydrocarbons and into a silica column under retention conditions which will retain aromatics and pass through saturated hydrocarbons;
    recovering the saturated hydrocarbons passed through the silica column;
    recovering the resins by displacing the resins from the cyano column with a polar displacement material;
    recovering the asphaltenes by displacing the asphaltenes from the cyano column with a displacement material having a greater polarity than the resin displacement material; and
    recovering the aromatics by displacing the aromatics from the silica column with a displacement material.

2. The method of claim 1, wherein the three part solvent mixture is comprised of about 13% to about 17% methanol, about 13% to about 17% acetone, and about 66% to about 75% chloroform.

3. The method of claim 1, wherein the mobile phase is hexane.

4. The method of claim 1, wherein the cyano column adsorbs the methanol and acetone, causing the asphaltenes to drop out of solution into the column, and retains the resins for a time sufficient to separate the resins from the unretained aromatics and saturated hydrocarbons.

5. The method of claim 1, wherein the silica column retains the chloroform for a time sufficient to separate the chloroform from the unretained saturated hydrocarbons before the chloroform is also passed through the column.

6. The method of claim 1, wherein the resins are displaced by backflushing the cyano column with a displacement material of a mixture of hexane and chloroform.

7. The method of claim 6, wherein the asphaltenes are displaced from the cyano column after the displacement of resins by backflushing with a displacement material having the composition of said three part solvent mixture.

8. The method of claim 1, wherein the aromatics are displaced by backflushing the silica column with a displacement material of chloroform.

9. The method of claim 8, further comprising regenerating the silica column after chloroform injection by injecting the same compound previously injected as the mobile phase with the solvated oil mixture.

10. The method of claim 1, further comprising comparing the weight of recovered fractions of asphaltenes, resins, aromatics, and saturated hydrocarbons with the weight of the starting sample to determine the fraction of the starting sample boiling lower than n-$C_{11}$ lost during removal of solvent from the recovered fractions.

11. A method of group type separation of oil or bitumen by high performance liquid chromatography, which comprises:
    solvating the oil with a three part solvent mixture of about 13% to about 17% methanol, about 13% to about 17% acetone, and about 66% to about 75% chloroform;
    injecting the solvated oil mixture with a mobile phase of hexane under retention conditions into a cyano bonded phase column which will retain toluene, acetone, asphaltenes and resins, and pass through aromatics and saturated hydrocarbons, said resins being retained for a time sufficient to separate the resins from the unretained aromatics and saturated hydrocarbons;

injecting the unretained saturated hydrocarbons and aromatics under retention conditions into a silica column which will retain aromatics and pass through saturated hydrocarbons;

recovering the saturated hydrocarbons unretained by the silica column;

recovering the resins by backflushing the cyano column with a mixture of hexane and chloroform;

recovering the asphaltenes by backflushing the cyano column with a displacement material having the composition of said three part solvent mixture; and recovering the aromatics by backflushing the silica column with chloroform.

* * * * *